United States Patent [19]

Avitt

[11] Patent Number: 5,074,287

[45] Date of Patent: Dec. 24, 1991

[54] CERVICAL TRACTION DEVICE

[76] Inventor: Frank Avitt, 637 Des Moines St., Des Moines, Iowa 50309

[21] Appl. No.: 548,868

[22] Filed: Jul. 6, 1990

Related U.S. Application Data

[62] Division of Ser. No. 376,234, Jul. 6, 1989, abandoned.

[51] Int. Cl.[5] .............................................. A61F 5/00

[52] U.S. Cl. ...................................... 128/75; 128/71; 128/845; 128/78

[58] Field of Search ...................... 128/78, 75, 73, 74, 128/71, 69, 87 B, 87 R, 84 C, 84.5, DIG. 23, 97.1

[56] References Cited

U.S. PATENT DOCUMENTS

| | | | |
|---|---|---|---|
| 2,658,506 | 11/1953 | Haskell | 128/75 |
| 2,808,049 | 10/1957 | Graham | 128/87 B |
| 2,984,238 | 5/1961 | Axtell et al. | 128/75 |
| 3,068,859 | 12/1962 | Treutelaar | 128/75 |
| 3,145,709 | 8/1964 | Pinegar | 128/84 R |
| 3,168,094 | 2/1965 | Siltamaki | 128/75 |
| 3,346,256 | 10/1967 | White | 272/123 X |
| 3,659,594 | 5/1972 | Schwab | 128/75 |
| 3,750,658 | 8/1973 | Dawson, Jr. et al. | 128/75 |
| 3,768,464 | 10/1973 | Greissing | 128/75 |

*Primary Examiner*—Robert A. Hafer
*Assistant Examiner*—Brian E. Hanlon

[57] ABSTRACT

A traction fulcrum arm is pivoted intermediate its ends on a support post and carries at one end a head halter tending to lift up on the patient's head in response to weights on the opposite end of the arm tending to pivot the arm downwardly. A motorized cam intermittently raises the weight end of the arm relieving the traction on the patient on a cyclical basis of 10 to 40 seconds. An an alternative to using the weights, a spring may be connected between the fulcrum arm and the frame to produce tractive forces. The desired angle of 45 degrees traction may be obtained through adjustment of the post vertically and the head halter carried on the arm while also adjusting the positioning of the chair towards and away from the head halter. The support post may also be pivoted away from the person in the chair for access in and out of the chair.

19 Claims, 3 Drawing Sheets

CERVICAL TRACTION DEVICE

This application is a division of Ser. No. 07/376,234 filed July 6, 1989, and abandoned July 7, 1990.

BACKGROUND OF INVENTION

Cervical disfunction and pain are commonly occurring problems associated with aging, immobility, emotional stress and physical fatigue. The most common disorders of the cervical area are acute and chronic sprain and strain, muscle spasms with inflammation, joint stiffness and herniated discs.

This problem is often treated by cervical traction, the objective of which is to restore normal pain-free movement. It is particularly desirable to apply traction with flexion, preferably when the angle of traction is approximately 45 degrees. Also ideally, traction is applied intermittently, as compared to continuous manual traction. The intermittent or rhythmic traction produces substantially more joint separation as is sustained by non-intermittent traction.

SUMMARY OF THE INVENTION

The cervical traction device of this invention accomplishes in a simplified fashion all of the objectives of preferred cervical traction therapy. The traction is applied over a period of time on an intermittent basis. The angle of tractive force is approximately 45 degrees. The device is easily adjustable to the particular patient regardless of the patient's size and height.

A fulcrum arm is pivoted at a point intermediate its ends to a support post and one end of the arm is connected through a head halter to the head of the patient who is sitting in a chair which is adjustably connected to the base of the stand. The other end of the fulcrum arm carries a weight which may be readily varied. A motorized cam engages the arm and on a 10 to 40 second cycle basis intermittently engages the arm to support the weight thereby relieving the traction on the patient followed by the tractive forces being applied to the patient due to the weight. As an alternative to using the weight, a spring may be connected to the arm to impose tractive force on the patient. This treatment is controlled by a timer.

The post supporting the fulcrum arm is adapted to pivot out of the way of the patient as needed.

DESCRIPTION OF THE PREFERRED EMBODIMENT

Figure 3:
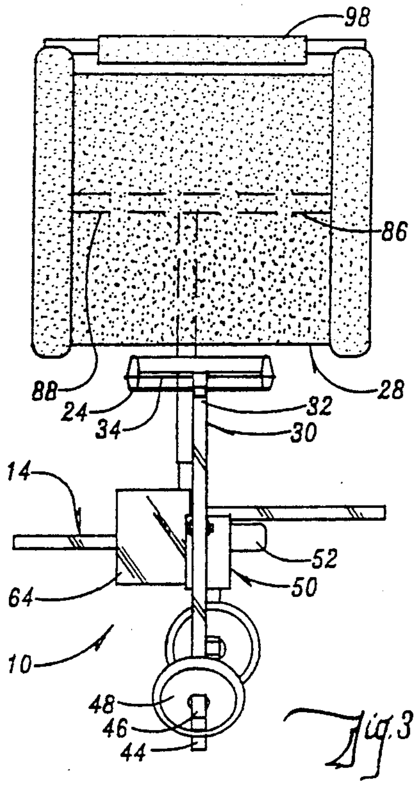
FIG. 3 is a top plan view thereof.
Figure 1:
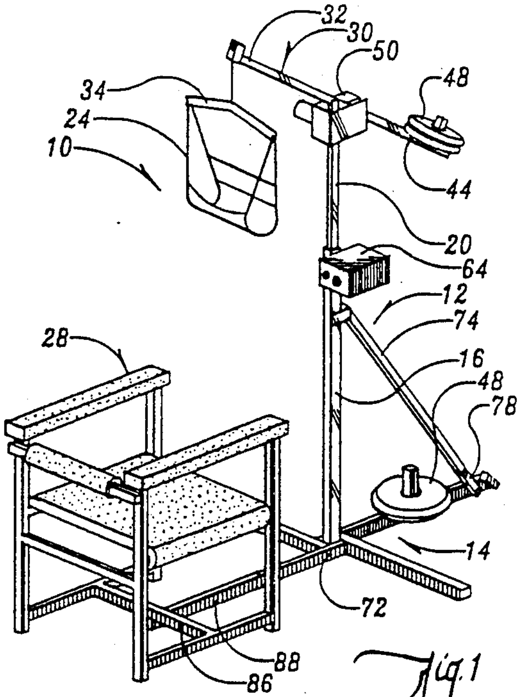
FIG. 1 is a perspective view of the cervical traction device.
Figure 9:
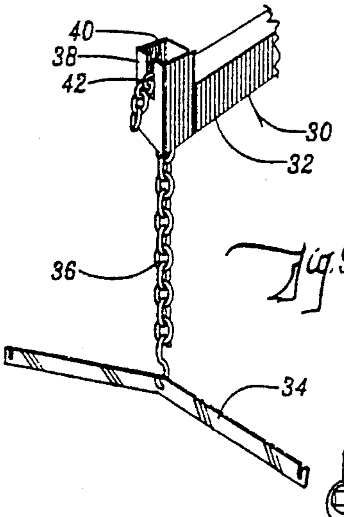
FIG. 9 is a fragmentary perspective view of the forward end of the fulcrum traction arm.

The cervical traction device of this invention is referred to generally in FIG. 1 by the reference numeral 10.

Figure 6:
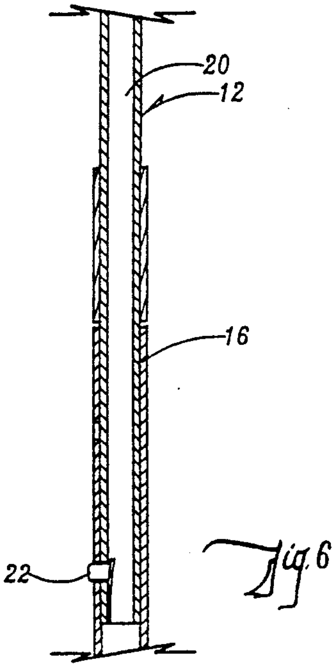
FIG. 6 is a cross-sectional view taken along line 6—6 in FIG. 5.

The traction device 10 includes a stand 12 having a base 14. The stand 12 includes a post 16 having a telescopic section 20 selectively interlocked by a spring-loaded detent 22 as seen in FIG. 6 to position the head halter 24 in the desired position relative to a person 26 sitting in a chair 28.

The upper post section 20 has a fulcrum traction arm 30 pivoted intermediate its ends. A forward end 32 supports a head halter spreader bar 34 through a chain 36 connected by a tube 38 having a slot 40 for engagement of a link 42 of the chain 36. Again, depending on the size of the patient 26 the head halter 24 may be positioned by adjustment of the chain 36.

The rear opposite end 44 of the fulcrum arm 30 includes an upstanding post 46 on which an apertured weight 48 is stacked. Additional weights 48 may be added to the post 46 as appropriate.

Figure 7:
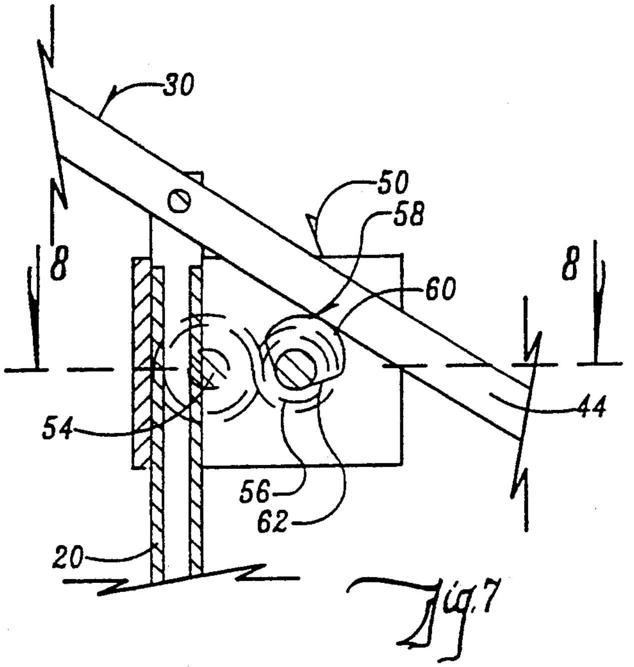
FIG. 7 is an enlarged fragmentary view of the cam in engagement with the fulcrum arm.
Figure 8:
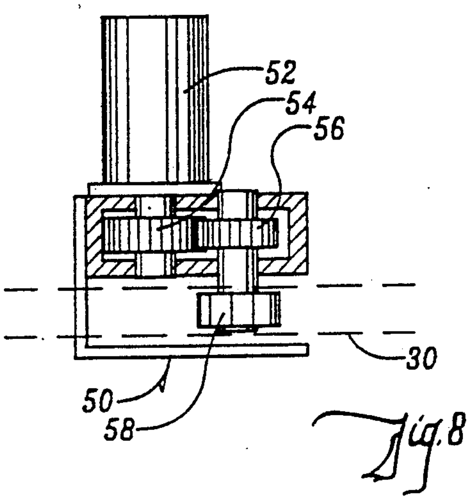
FIG. 8 is a cross-sectional view taken along line 8—8 in FIG. 7.

A cam means 50 is provided which includes a motor 52 which through a gear 54 drives a reducing gear 56 which in turn is connected to a cam 58 which engages the lower side of the fulcrum arm 30 as seen in FIG. 7. The cam 58 has an area 60 which has a larger radius than the opposite side 62 and thereby when the larger radius area 60 engages the arm 30 the weight 48 is supported removing traction from the patient 26 and conversely when the smaller radius 62 of the cam 58 engages the arm 30 tractive force is applied to the patient through the head halter 24.

A control unit 64 is mounted on the post 16 and includes a variable speed control 66 and a timer 68 whereby the intermittent traction can be varied between 10 to 40 second cycles. The duration of the treatment can be varied as desired with 15 minutes being preferred.

The post 16 is pivoted at 70 to a base 72 and is held erect by a support brace 74 extending from the post to a base leg 76. An over center link connection 78 is provided which allows the post 16 to pivot to the dash-line position of FIG. 2 when the link 78 is pivoted out of the plane of the brace 74 and moves against the stop 80. This allows the patient to enter and leave the chair 28. When the brace is in the solid line position of FIG. 2 the post 16 is vertically upright and the link 78 is in the plane of the support brace 74 and is held in this position by stop plate 82.

The leg 76 also includes an upstanding pin 84 which stores extra weights 48.

Figure 2:
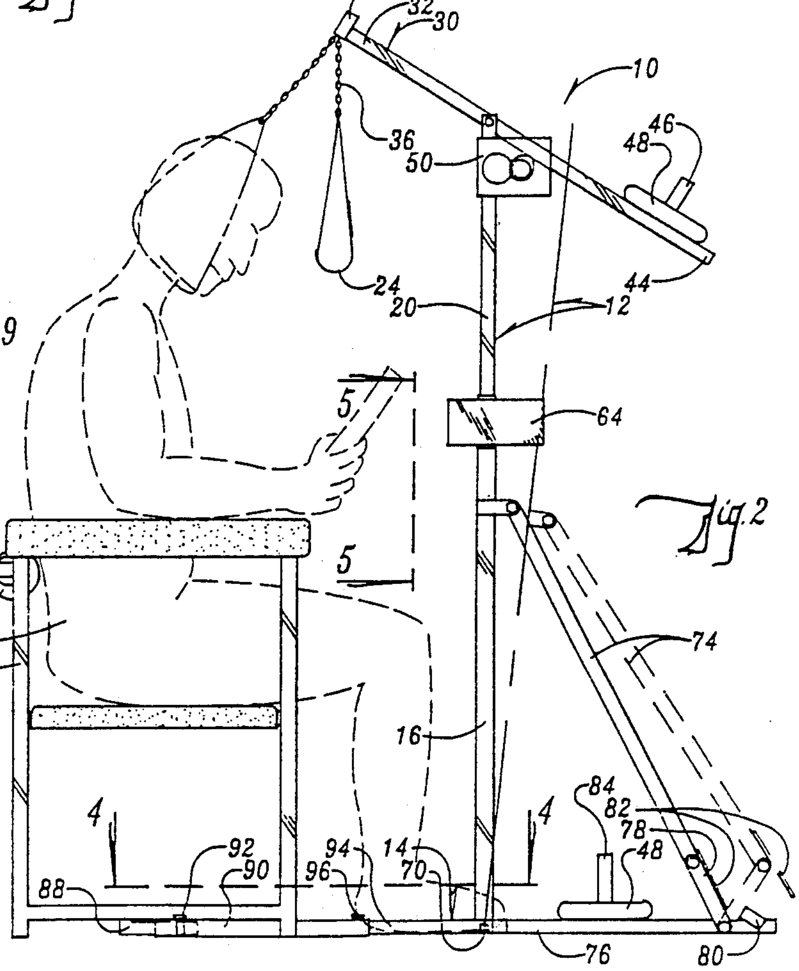
FIG. 2 is a side elevation view thereof.
Figure 4:
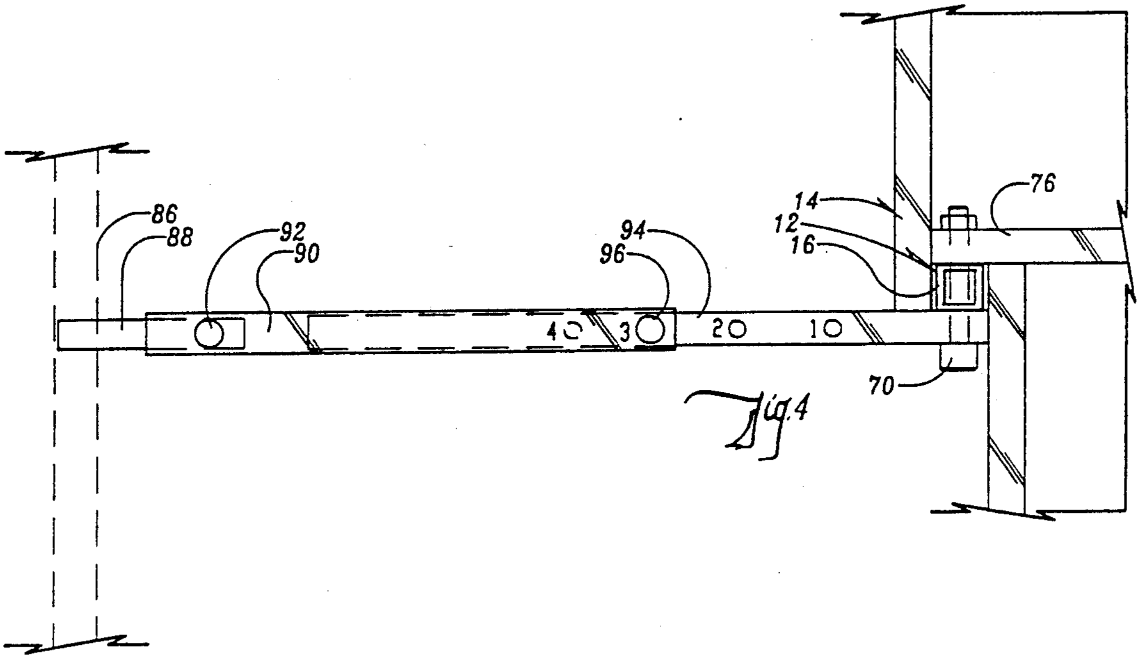
FIG. 4 is a cross-sectional view taken along line 4—4 in FIG. 2.
Figure 5:
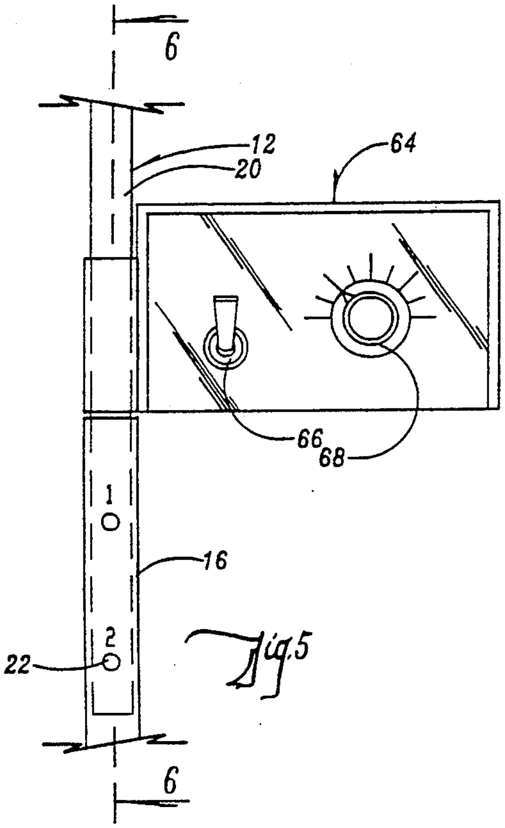
FIG. 5 is a cross-sectional view taken along line 5—5 in FIG. 2.

The chair 28 has a cross-member 86 at floor level which has a forwardly extending tubular member 88 telescopically received in a base leg 90 and locked thereto by a pin 92 as seen in FIG. 2. The leg member 90 telescopically engages base leg 94 and is adjustably locked thereto by removable pin 96 thereby allowing the patient to be positioned appropriately for the desired tractive angle when the tractive forces are applied.

The patient should have as a reference point the back member engaging the person's back at waist level. The back or reference member 98 serves two purposes. When in contact with the patient's back, the upper part of the patient's body is upright. Since it is desirable that in proper usage of the device the chain portion 36 between the tube 38 and head halter 24 is at 45 degrees, it is necessary that the patient's back is in engagement with the back member 98, thus insuring that the chain portion, halter and head is substantially and constantly 45 degrees with respect to the patient's back. Also, the entire chair is adjustable toward and away from the post 16 and the post section 16 is vertically adjustable. Likewise the effective length of the halter chain is adjustable. Once a patient knows or learns the proper adjustments, he can self-adjust the device. Once adjusted and by sitting in the chair so that he contacts the back member 98, he will know the direction of force will be at 45 degrees. Therefore, a single traction device may be used by several patients regardless of their individual sizes.

It is thus seen in use that the 45 degree head position can be obtained for all patients by selective positioning of the chair 28 relative to the head halter 24 and the halter itself may be appropriately positioned by adjustment of the chain 36 connected to the forward end 32 of the fulcrum arm 30. The supporting post 16 is adjustable vertically as desired. The frequency of the intermittent tractive forces may be varied by operation of the control 66 in a range of 10 to 40 second cycles. The length of treatment can be varied through operation of the timer 68. It is also noted that the head halter spreader bar 34 is angular in shape thereby allowing greater space between the person's head and the bar at the point the chain 36 is connected to the bar.

Figure 10:
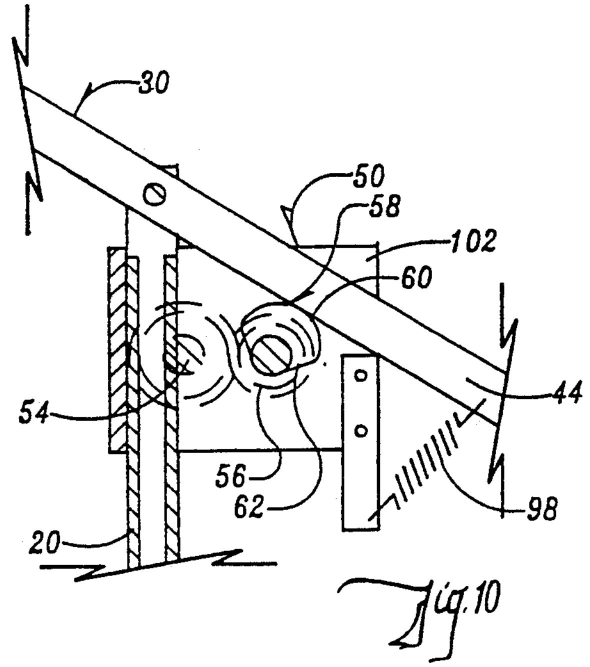
FIG. 10 is a view similar to FIG. 7 but showing an alternative embodiment wherein a spring is utilized in lieu of a weight.

An alternative embodiment to use of the weight 48 is shown in FIG. 10 wherein a spring 98 is used which extends between the rear opposite end 44 of the fulcrum arm 30 and a bracket 100 attached to the housing 102 of the cam means 50. This is a simplified system when extreme accuracy afforded by the individual weights 48 is not required.

I claim:

1. A cervical traction device comprising,
- a traction fulcrum arm pivotally mounted intermediate opposite ends on a support,
- a head halter connected to one end of said arm,
- a counter balance means connected to the opposite end of said arm to pivot it downwardly,
- a cam means engaging said arm for intermittently supporting the opposite end of said arm whereby intermittent traction is applied to said head halter,
- a chair carried on said support so that a user sitting in the chair will be beneath and facing said one end of said fulcrum arm connected to the halter,
- said chair having a reference member engageable with a user sitting upright in said chair,
- said support being vertically adjustable in height,
- said head halter being adjustably spaced from said one end of said arm,
- and said chair being horizontally adjustable positioned relative to said support such that a line of traction from said one end of said arm to said head halter when on a user is substantially at a 45 degree angle to a vertical line through said one end of said arm whereby a user sitting upright in said chair and having his head bent forwardly toward said one end of said fulcrum arm will have traction applied substantially exclusively to the cervical area of the user and while said cervical area is in flexion.

2. The structure of claim 1 wherein said support is further defined as being a stand having an upstanding post on which said arm is pivoted.

3. The structure of claim 2 wherein said cam means is mounted on said post adjacent said arm.

4. The structure of claim 3 wherein said cam means is positioned under said opposite end of said arm for intermittently raising and lowering said opposite end of said arm.

5. The structure of claim 4 wherein said cam means includes a motor operatively connected to a cam for rotating said cam.

6. The structure of claim 5 wherein said cam has a circumferential surface with a varying radius engaging said arm.

7. The structure of claim 6 wherein said varying radius gradually changes from a large radius to a small radius and when said cam surface having said large radius engages said arm said opposite end of said arm is raised and when said smaller radius surface engages said arm said opposite end of said arm is lowered applying traction to said head halter.

8. The structure of claim 5 wherein said cam means includes a variable speed control for varying the number of cycles of traction over a period of time.

9. The structure of claim 8 wherein said cam means includes a timer control for varying the period of time said motor is operative thereby varying the operative traction treatment period.

10. The structure of claim 1 wherein said head halter is adjustably connected to said one end of said arm by a chain having a plurality of links.

11. The structure of claim 2 wherein said post is further defined as being pivotally mounted on a base and adjustment means allows said post to be pivoted between an upright position to an angular position towards the opposite end of said bar for ease of positioning a person under said head halter.

12. The structure of claim 11 wherein the pivoting of said post is further defined by a support brace extending between said post and said base, and said brace being effectively adjustable in length.

13. The structure of claim 12 wherein said length of said brace is made adjustable by it including an over center connection to said base whereby in one position the effective length of said brace is less and said post is in said angular position and in a second brace position said effective length is greater and said post is in said upright position.

14. The structure of claim 13 wherein stop means are provided for limiting pivotal movement in said over center connection between said post and said base in said brace first and second positions.

15. The structure of claim 2 wherein said post is mounted on a base and a chair is adjustably connected to said base for selectively positioning the user to said head halter.

16. The structure of claim 15 wherein said adjustable connection between said base and chair include a telescopic member.

17. The structure of claim 1 wherein said counter balance means is further defined as weight means connected to said opposite end of said arm, said weight means includes an upstanding pin on said opposite end of which a weight having a center opening is mounted by said pin being received in said center opening.

18. The structure of claim 17 wherein said post is connected to a base and a storage pin is provided on said base for holding weights not being used on said opposite end of said arm.

19. The structure of claim 1 wherein said counter balance means is further defined as a spring means connected to said opposite end of said arm and operatively extending to said support.

* * * * *